(12) United States Patent
Sakairi et al.

(10) Patent No.: US 9,678,093 B2
(45) Date of Patent: Jun. 13, 2017

(54) AUTOMATIC ANALYZER

(71) Applicants: HITACHI HIGH-TECHNOLOGIES CORPORATION, Tokyo (JP); ROCHE DIAGNOSTICS OPERATIONS, INC., Indianapolis, IN (US)

(72) Inventors: Susumu Sakairi, Tokyo (JP); Katsuhiro Kambara, Tokyo (JP); Stephan Sattler, Starnberg (DE); Reinhold Kraemer, Peissenberg (DE)

(73) Assignees: Hitachi High-Technologies Corporation, Tokyo (JP); Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/909,782

(22) PCT Filed: Jun. 27, 2014

(86) PCT No.: PCT/JP2014/067094
§ 371 (c)(1),
(2) Date: Feb. 3, 2016

(87) PCT Pub. No.: WO2015/025616
PCT Pub. Date: Feb. 26, 2015

(65) Prior Publication Data
US 2016/0161521 A1   Jun. 9, 2016

(30) Foreign Application Priority Data

Aug. 20, 2013  (JP) ................................. 2013-170046

(51) Int. Cl.
*G01N 35/10*  (2006.01)
*G01N 35/00*  (2006.01)
(Continued)

(52) U.S. Cl.
CPC ... *G01N 35/1002* (2013.01); *G01N 35/00663* (2013.01); *G01N 35/025* (2013.01);
(Continued)

(58) Field of Classification Search
CPC .. G01N 2035/0405; G01N 2035/00287; B01L 3/50825
See application file for complete search history.

(56) References Cited

U.S. PATENT DOCUMENTS

2004/0057872 A1* 3/2004 Shibuya ............. G01N 35/1002
                                                      422/64
2010/0080732 A1  4/2010 Mototsu et al.
(Continued)

FOREIGN PATENT DOCUMENTS

EP   2 192 411 A1   6/2010
JP   2010-078510 A  4/2010
(Continued)

OTHER PUBLICATIONS

International Search Report of PCT/JP2014/067094.
(Continued)

*Primary Examiner* — P. Kathryn Wright
(74) *Attorney, Agent, or Firm* — Mattingly & Malur, PC

(57) ABSTRACT

An automatic analyzer provided with a roller and a reagent container shoulder presser at the position where an operator inserts a reagent container into the automatic analyzer. The reagent container is pushed while the lid of the reagent container is made to touch the upper side of the roller and the shoulder presser is made to touch the shoulder of the reagent container, and the application of upward force to the lid causes the lid of the reagent container to be half open, after which the reagent container is inserted in the analyzer.

11 Claims, 22 Drawing Sheets

(51) Int. Cl.
*G01N 35/02* (2006.01)
*B01L 3/00* (2006.01)
*G01N 35/04* (2006.01)

(52) U.S. Cl.
CPC ..... *B01L 3/50825* (2013.01); *G01N 2035/00287* (2013.01); *G01N 2035/00673* (2013.01); *G01N 2035/0405* (2013.01); *G01N 2035/0443* (2013.01)

(56) References Cited

U.S. PATENT DOCUMENTS

2012/0186200 A1* 7/2012 Jones .................. G01N 35/04
                                                        53/471
2012/0301359 A1 11/2012 Kraemer et al.
2012/0328475 A1 12/2012 Sakairi et al.

FOREIGN PATENT DOCUMENTS

| JP | 2011-027663 A | 2/2011 |
| WO | 2011/074472 A1 | 6/2011 |
| WO | 2011/108134 A1 | 9/2011 |

OTHER PUBLICATIONS

International Preliminary Report on Patentability received in corresponding International Application No. PCT/JP2014/067094 dated Mar. 3, 2016.
Extended European Search Report received in corresponding European Application No. 14837621.3 dated Mar. 15, 2017.

* cited by examiner

AUTOMATIC ANALYZER

TECHNICAL FIELD

The present invention relates to an automatic analyzer used for chemical analyses such as a biochemical analysis and an immunity analysis in clinical examinations.

BACKGROUND ART

An automatic analyzer used for chemical analyses such as a biochemical analyzer and an immunity analyzer in clinical examinations performs measurements by holding plural kinds of reagents in a reagent storage according to analysis items, drawing a given amount of reagent from a reagent container in the reagent storage at the time of use and mixing the reagent with a sample. A normal reagent container is provided with a lid for preventing evaporation, deterioration and leakage of the reagent in an opening of the container for drawing the reagent therefrom. When a new reagent is charged into the apparatus, an operator sets the reagent container at a predetermined position in the reagent storage after opening the lid. In this case, the opening of the reagent container is constantly opened, evaporation, deterioration and so on of reagents may occur in some reagents which are stored in the reagent storage for a long period of time. Moreover, when the operator takes the reagent container out from the reagent storage, liquid leakage may occur in the case where the operator accidentally knocks over the reagent container.

In Patent Literature 1, an automatic analyzer including a reagent lid opening/closing mechanism capable of opening and closing lids of reagent containers in a reagent storage is described. In the apparatus, an operator charges reagents in the reagent storage in a state where openings of the reagent containers are sealed. When the reagent is used, the lid of the reagent container is automatically opened, and the reagent can be drawn from the opening. As the opening can be sealed again after the reagent is used, it is possible to reduce the possibility of deterioration and leakage of the reagent.

In Patent Literature 2, there is disclosed an apparatus capable of drawing a reagent in a reagent container by performing a first operation of releasing the sealed state between a lid member and an opening by using a rotating movement of a reagent disc in a reagent storage and a second operation of moving the lid member to a place where the opening is not covered in the state where the sealed state is released as a method of opening and closing the lid of the reagent container mounted on the apparatus.

CITATION LIST

Patent Literature

Patent Literature 1: WO-2011-074472
Patent Literature 2: JP-A-2010-78510

SUMMARY OF INVENTION

Technical Problem

Generally, a lid of a reagent container is totally sealed before starting use in many cases for preventing evaporation or deterioration of a reagent housed in the reagent container and liquid leakage during transport, and a large force for releasing the sealed state may be necessary for opening the lid.

When trying to open the sealed lid of the reagent container in the middle of analyzing processing by the reagent lid opening/closing mechanism according to Patent Literature 1, it is necessary to have a power source which can exert enough power to open the sealed opening for surely opening the lid. The larger the drive force of the power source becomes, the larger the size of the power source may be, therefore, the reagent lid opening/closing mechanism is also increased in size, which makes the installation in a limited space in the reagent storage difficult.

In the case where the lid is opened by using the rotating movement of the reagent disc as described in Patent Literature 2, a large load may be applied to the rotating power source of the reagent disc for opening the lid which is tightly sealed, and it may be necessary to increase the size of the structure of the reagent storage itself. If the drive force of the power source is not sufficient, there are dangers that analysis is hard to be performed as the lid is not capable of being opened, and that the apparatus is damaged.

In view of the above problems, an object of the present invention is to provide an automatic analyzer capable of releasing the sealed state of a lid of a reagent container while maintaining the saved space of the structure without applying a load on the apparatus.

Solution to Problem

The structure of the present invention for solving the above problems is as follows. That is, an automatic analyzer includes a reagent storage including plural slots capable of storing reagent containers each having a main body housing a reagent used for analysis, an opening provided on a top of the main body and a lid portion having a sealing member for sealing the opening by being inserted into the opening, a reagent loader mechanism capable of carrying the reagent container in the reagent storage from the outside, a processing mechanism executing dispensing or stirring processing to the reagents stored in the reagent storage, a reagent container lid opening/closing mechanism provided in the reagent storage, opening and closing lids of the reagent containers set in the reagent storage before and after the processing mechanism performs the processing and a reagent container lid half-open mechanism allowing the lids of the reagent containers to be set in the reagent loader mechanism to be in a half-open state.

Advantageous Effects of Invention

When adopting the above structure according to the present invention, the sealed state of the lids of the reagent containers can be released to be in the half-open state by the operation for setting the reagent containers in the reagent loader mechanism by the operator, therefore, a load applied to the reagent container lid opening/closing mechanism for opening and closing the lids of the reagent containers during analysis can be reduced.

DESCRIPTION OF EMBODIMENTS

Hereinafter, an embodiment of the present invention will be explained with reference to the drawings.

Figure 22:
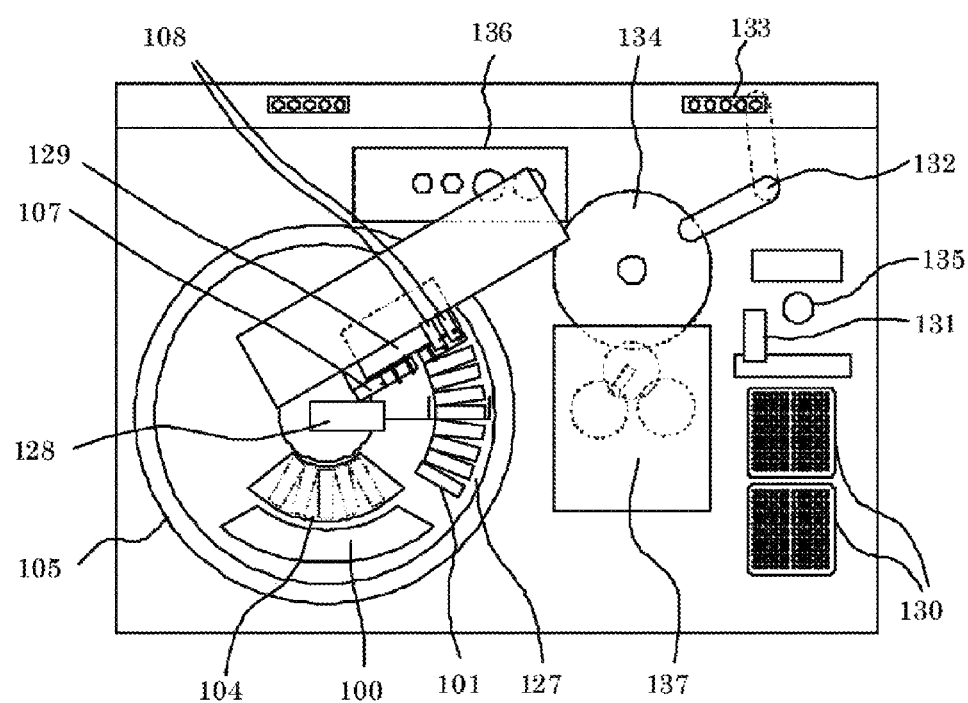
FIG. 22 is a top view showing the entire automatic analyzer according to the present invention.

As an example of an apparatus including a reagent container lid half-open mechanism according to the present invention, the entire structure of an automatic immunity analyzer and the flow to the detection will be explained. FIG. 22 shows a top view of the automatic immunity analyzer.

The automatic analyzer mainly includes a reagent cooler 105 having a reagent loader mechanism 104 which automatically carries in/out reagent containers to/from the inside, a magnetic particle stirring device 107 stirring reagents (particularly reagents containing magnetic particles) in the reagent cooler, a magazine 130 having plural consumables necessary for analysis (for example, reaction containers, sample dispensing chips and the like), a reaction container/sample dispensing chip conveyance device 131 carrying the consumables on the magazine 130 to suitable positions, a sample dispensing device 132 dispensing a predetermined amount of a sample into the reaction container from a sample 133 on a conveyance line in a state where the sample dispensing chip is mounted, a reaction vessel 134 holding the reaction containers which house samples with a predetermined temperature, a reagent dispensing device 108 which draws a predetermined cooler reagent in the reagent cooler and discharges the reagent in the reaction container, a reaction liquid stirring device 135 stirring the sample and the reagent in the reaction container for mixing them, a reaction liquid cleaning device 136 removing components other than a measurement target component inside the reaction container and a detecting section 137 for measuring a fixed amount of measurement target component in reaction liquid.

The reagent cooler 105 is sealed by a lid (not shown) on an upper surface and the lid is partially provided with an opening through which the reagent loader mechanism 104, a stirrer of the magnetic particle stirring device 107 and a probe of the reagent dispensing device 108 can pass. A reagent container lid half-open mechanism 100 is provided on the lid of the reagent cooler 105, which can release the sealed state of lids of the reagent container before carrying the reagent in the reagent cooler. In the reagent cooler 105, a reagent disc 127 including plural slots in which the reagent containers can be set is provided, and an arbitrary reagent container can be carried to access positions of respective mechanisms by rotationally moving the reagent disc. A reagent container moving device 128 can move the reagent containers between the reagent loader mechanism 104, the slots of the reagent disc 127 and a stirring position by the magnetic particle stirring device 107. A reagent container lid opening/closing device 129 can open the lids of the reagent container at a suitable timing before being processed by the magnetic particle stirring device 107 or the reagent dispensing device 108, and can close the lids after using the reagents and after the processing is completed.

As a preparation before starting the analysis, reagent containers 101 used for analysis are set on the reagent disc 127 inside the reagent cooler 105. The reagent container lid half-open mechanism 100 is provided on a path through which the reagent container passes when setting the reagent container in the reagent loader mechanism 104 in the state where the reagent loader mechanism 104 is on the lid of the reagent cooler 105. The operator sets the reagent container 101 on the reagent loader mechanism 104 through the reagent container lid half-open mechanism 100.

After that, the reagent loader mechanism 104 is moved downward to be returned to the reagent cooler 105, and the reagent containers 101 placed on the reagent loader mechanism 104 are moved to the slots of the reagent disc 127 by the reagent container moving device 128. The reagent containers 101 moved to the reagent disc 127 are used for analysis processing. The upper and lower movements of the reagent loader mechanism 104 may be performed from a screen for operating the automatic analyzer as well as may be performed by switching operation by installing a switch in the vicinity of the reagent loader mechanism 104.

After the reagent containers 101 necessary for analysis have been charged, the analysis processing is started.

First, the reaction containers mounted on the magazine 130 are moved to the reaction vessel 134 by the reaction container/sample dispensing chip conveyance device 131, and further the sample dispensing chip is moved to a position where the sample dispensing chip is attached to a tip of the probe of the sample dispensing device 132. The reaction vessel 134 can be horizontally and rotationally driven in a state of holding plural reaction containers. The reaction vessel 134 rotates to a reagent dispensing position and the reagents in the reagent container 101 are first dispensed into the reaction containers. The processing to the dispensing of the reagents in the reagent container 101 is omitted as it is described in Embodiment 1. At the same time, the sample dispensing device 132 mounting the sample dispensing chip draws samples mounted on the sample rack 133, the reaction containers into which the reagents are dispensed are moved to a sample dispensing position by the rotation of the reaction vessel 134, and the samples are dispensed into the reaction containers by the sample dispensing device 132. After that, the temperature of the reaction containers is kept on the reaction vessel 134 for a certain period of time for making the reagents and the samples reacting inside the reaction containers. After that, the reaction containers are moved to the reagent dispensing position again and magnetic particles in the reaction container 101 are dispensed by the reagent dispensing device 108. Then, after the reaction vessel 134 is rotated, the reaction containers on the reaction vessel 134 are moved to the reaction liquid stirring device 135 by the reaction container/sample dispensing chip conveyance device 131, where the magnetic particles and the reagents/samples allowed to react for a certain period of time are stirred by the reaction liquid stirring device 135. The reaction containers the stirring of which have been completed are returned to the reaction vessel 134 by the reaction container/sample dispensing chip conveyance device 131 and are allowed to react for a certain period of time on the reaction vessel 134, then, the reaction liquid (reagent/sample/magnetic particles) in the reaction containers is introduced into the detecting section 137 to perform detection. Here, cleaning processing of reaction liquid may be performed for removing impurities contained in the reaction liquid by the reaction liquid cleaning device 136 before the detection processing according to analysis items. A series of processing can be performed in succession.

Embodiment 1

Figure 1:
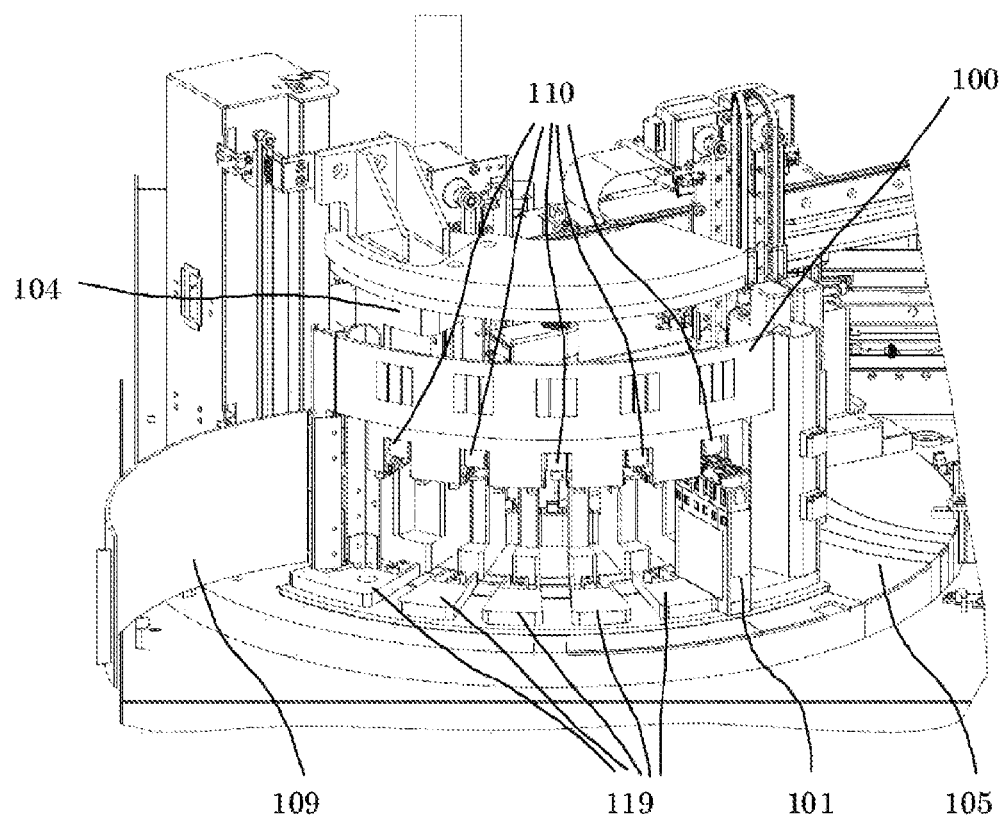
FIG. 1 is a perspective view showing a vicinity of a reagent container lid half-open mechanism according to the present invention.

FIG. 1 is a perspective view showing a vicinity of the reagent container lid half-open mechanism 100 of the automatic analyzer according to an embodiment of the present invention. Although a cover for preventing the access of an operator during analysis operation is originally provided from an upper surface to a front surface of the apparatus, the cover is not shown in all drawings for making a mechanical section relating to the present invention easier to see. The explanation will be made by citing an automatic analyzer using a magnetic particle reagent for analyzing samples as an example, and there is no limitation in kinds of reagents.

Figure 2:
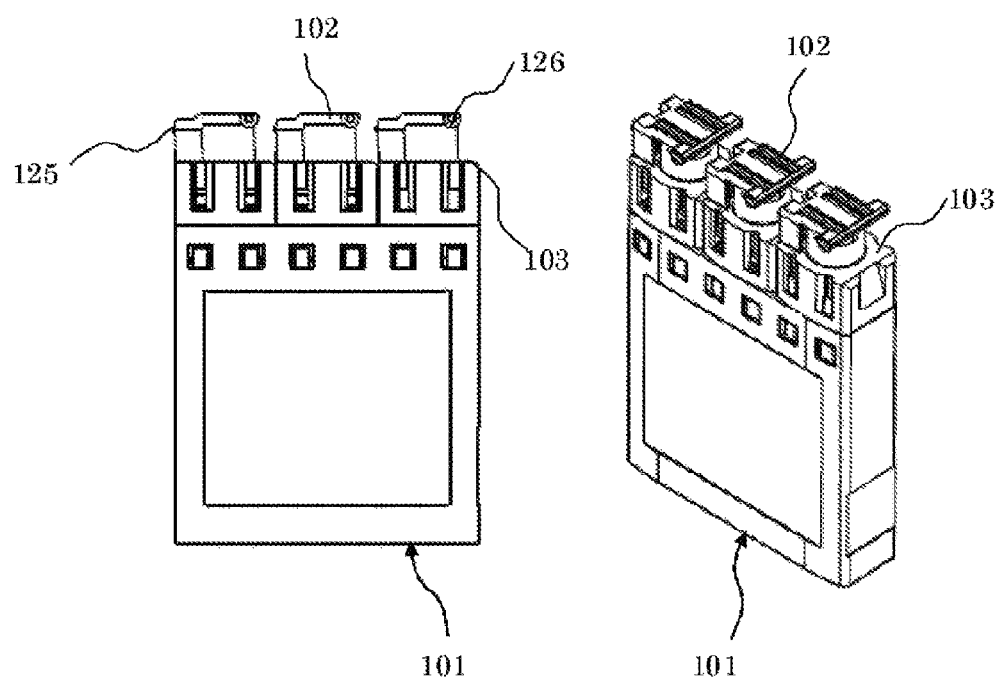
FIG. 2 is a view showing a state in which lids of a reagent container are closed.
Figure 3:
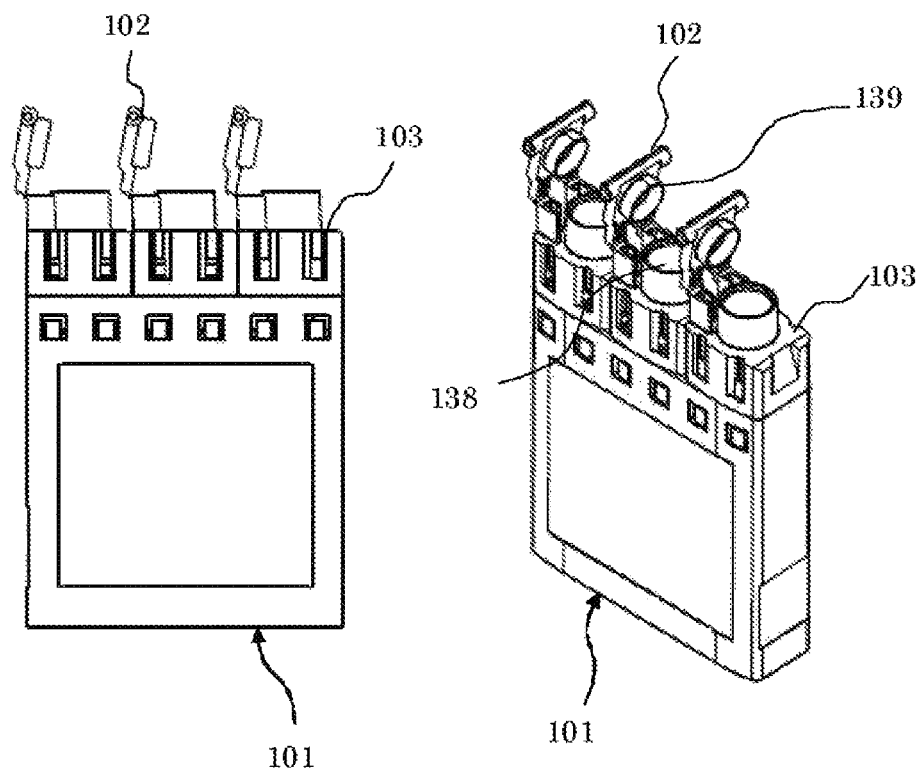
FIG. 3 is a view showing a state where the lids of the reagent container are fully opened.
Figure 4:
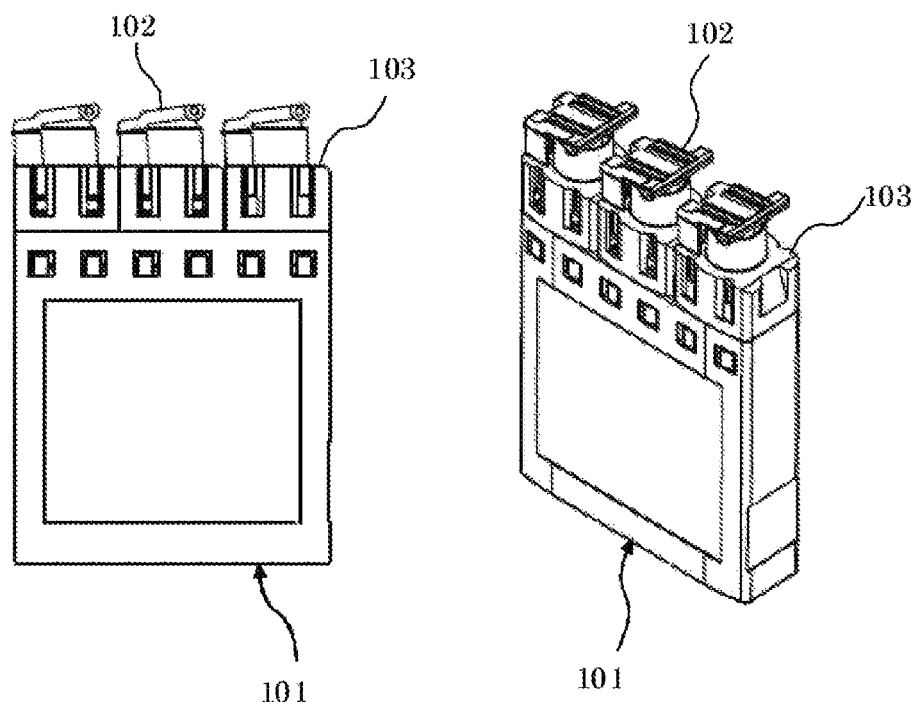
FIG. 4 is a view showing a state in which the lids of the reagent container are half opened.

FIG. 2 to FIG. 4 shows an example of the reagent container 101 to which the present invention is applied. In the reagent container 101, three containers make one set, for example, a magnetic particle solution and two kinds of reagents make one set. Each container includes a main body housing a reagent, an opening 138 through which access to the reagent can be obtained and a lid portion 102 capable of sealing the opening 138. An outer shape of the entire reagent container 101 is an approximately rectangular parallel piped shape having shoulder portion 103, and three openings 138 are aligned on an upper side of the shoulder portion 103 so as to project upward. A round-bar shaped projection 126 is provided on one end of each lid portion 102, which project toward a side surface direction of the reagent container 101 with respect to the lid portion for enabling opening/closing movements by the reagent container lid opening/closing device 129.

FIG. 2 shows the reagent container in a sealed state. The opening 138 is sealed by the lid portion 102 in the initial state. A sealing member 139 capable of being inserted to seal the opening 138 is provided in the lid portion for positively sealing the opening 138. As the sealing member 139 normally has almost the same shape as the opening 138, it is necessary to pull the lid portion in a direction rotationally moving upward by being hooked by the projection and to pull out the sealing member 139 inserted into the opening 138 for releasing the sealed state, a relatively large force is required.

FIG. 3 shows the reagent container in an opened state. The lid portion 102 is opened from the projection 126 side by being rotated around a hinge 125 as a rotation axis. At this time, the sealing member 139 is removed from the opening 138 completely and the lid portion 102 is opened at a wide angle around the hinge 125.

FIG. 4 shows a drawing of the reagent container the lid portion 102 of which is in a half-open state. In the half-open state, the sealing member 139 is removed from the opening 138 and the sealed state of the opening 138 is released, however, the lid portion 102 covers the opening 138, which prevents evaporation, deterioration and so on of reagents inside the reagent container. One of the objects of the present invention is to allow the lid portion 102 of the reagent container 101 from the sealed state to the half-open state before carrying the reagent container into the reagent cooler. The half-open state in the present invention indicates the state shown in FIG. 4.

In the automatic analyzer to which the present invention is applied, the analysis is performed in a state where the reagent container 101 housing reagents is mounted inside the reagent cooler 105 having a cool storage function. In the reagent cooler 105, the reagent loader mechanism 104 in which the plural sets of reagent containers 101 can be set, the reagent disc 127 (shown in FIG. 22) on which the plural sets of reagent containers 101 can be mounted, the reagent container moving device 128 (shown in FIG. 22) which can move the reagent containers 101 between the reagent loader mechanism 104 and the reagent disc 127, the reagent container lid opening/closing device 129 (shown in FIG. 22) which can open and close the lid portions 102 of the reagent container 101 in analysis processes and so on are provided.

Figure 5:
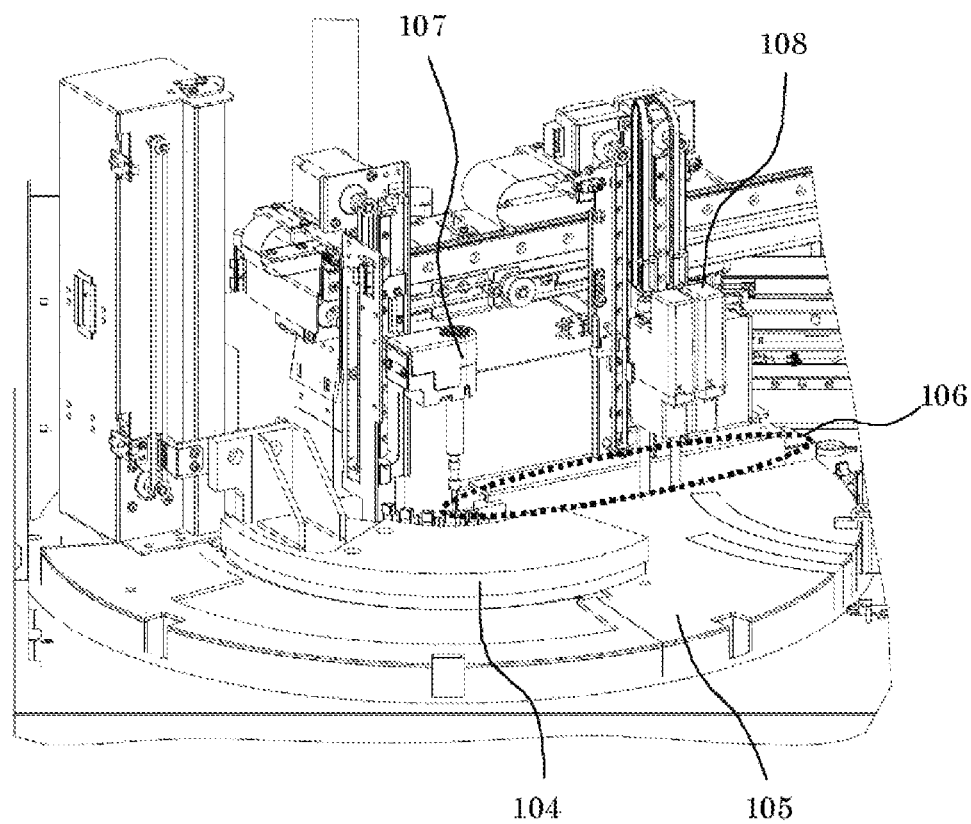
FIG. 5 is a perspective view showing a structure of a vicinity of a reagent container lid half-open mechanism of an automatic analyzer according to an embodiment of the present invention, showing a state where a reagent setting section moves downward (the reagent container lid half-open mechanism is not shown).
Figure 6:
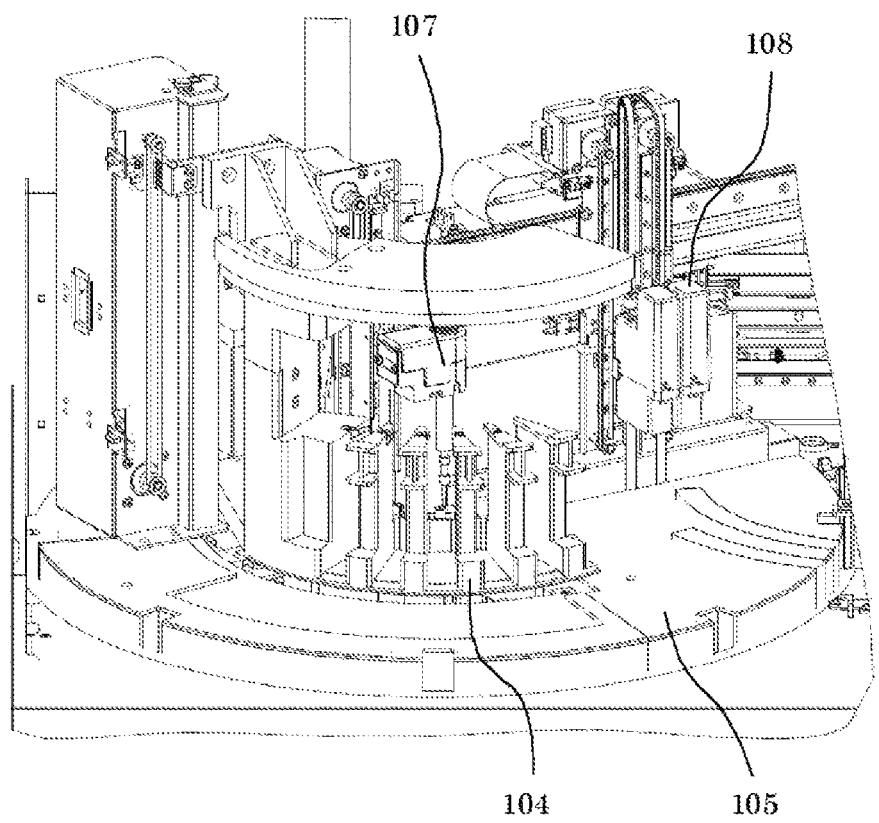
FIG. 6 is a perspective view showing a structure of a vicinity of the reagent container lid half-open mechanism of the automatic analyzer according to the embodiment of the present invention, showing a state where the reagent setting section moves upward (the reagent container lid half-open mechanism is not shown).
Figure 7:
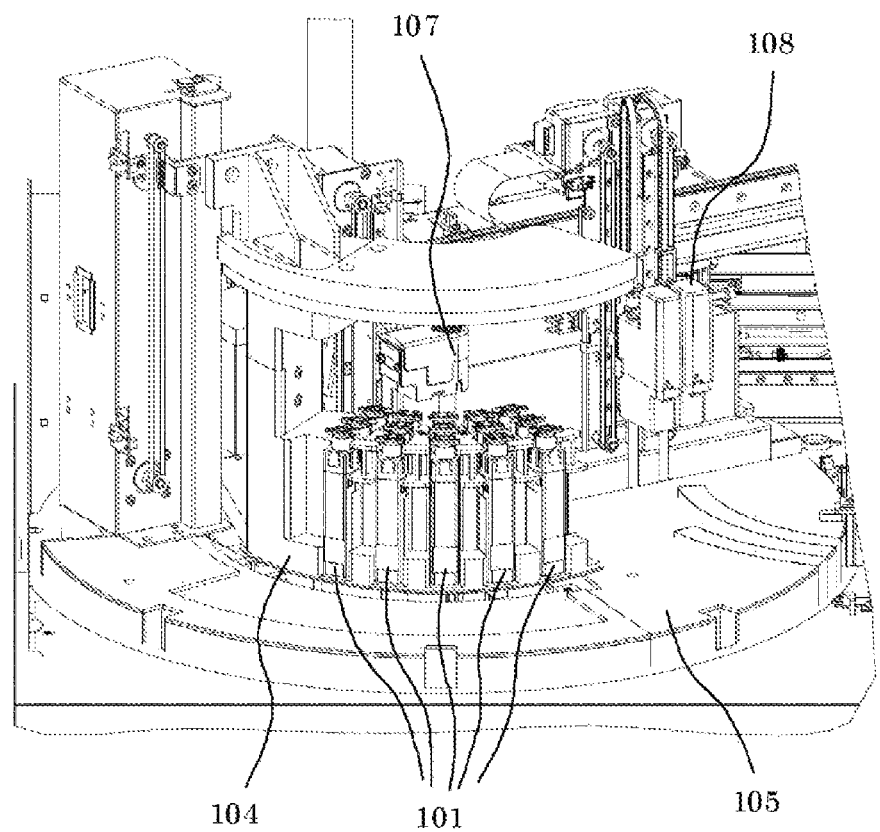
FIG. 7 is a perspective view showing a structure of a vicinity of the reagent container lid half-open mechanism of the automatic analyzer according to the embodiment of the present invention, showing a state where reagent containers are mounted in the state where the reagent setting section moves upward (the reagent container lid half-open mechanism is not shown).

The reagent loader mechanism 104 is used for mounting the reagent container 101 inside the reagent cooler 105. As shown in FIG. 5 and FIG. 6 (the reagent container lid half-open mechanism is not shown), the reagent loader mechanism 104 is configured to be vertically movable. In a state where the reagent loader mechanism 104 is in the bottom position (FIG. 5), the reagent cooler 105 can be sealed for improving cool storage efficiency and preventing intrusion of dirt and dust. In a state where the reagent loader mechanism 104 is in the top position (FIG. 6), the reagent containers 101 can be set as shown in FIG. 7. After that, the reagent containers 101 set in the reagent loader mechanism 104 are moved to the reagent disc 127 by the reagent container moving device 128.

In the outside of the reagent cooler 105, the magnetic particle stirring device 107, the reagent dispensing device 108 and so on are provided. It is possible to have access to the inside of the reagent container 101 mounted on the reagent disc 127 at a stirring and dispensing position 106.

The reagent disc 127 can be rotationally driven in a horizontal direction. In the analysis processes, the mounted reagent container 101 is moved to the stirring and dispensing position 106, magnetic particles inside the reagent container 101 are stirred by the magnetic particle stirring device 107 and reagents housed in the reagent container 101 are separated and dispensed by the reagent dispensing device 108 in a state where the lid portions 102 of the reagent container 101 are opened by the reagent container lid opening/closing device 129. The lid portions 102 of the reagent container 101 in which the stirring of magnetic particles and separation/dispensing of reagents have been completed are closed by the reagent container lid opening/closing device 129.

As described above, the analysis processes include a process of opening and closing the lid portion 102 of the reagent container 101 by the reagent container lid opening/closing device 129. In this process, it is desirable to open the lid portions 102 of the reagent container 101 only when needed and to close the lid portions 102 other than these cases for preventing evaporation or deterioration of reagents.

However, to open the lid portions 102 of the reagent container 101 inside the apparatus from the completely closed state or to close the lid portions 102 completely from the opened state applies a large load on the reagent container lid opening/closing device 129 and relating members, which has a possibility of not being capable of opening/closing the lid portions 102 completely or a possibility of damaging the reagent container lid opening/closing device 129 and the relating members.

In the embodiment, the reagent container lid half-open mechanism is provided in front of the reagent loader mechanism 104 so that the sealed state of the lid portions 102 is released and in the half-open state (FIG. 4) at the time of setting the reagent container 101 in the reagent loader mechanism 104. The mechanism is configured to allow the lid portions 102 to be in the half-open state with a force as small as possible as well as with a space as small as possible on the assumption that the operator pushes the reagent container 101. Accordingly, evaporation or deterioration of reagents can be suppressed to some degree even when the reagents are held in the reagent cooler for a long period of time, and the opening/closing of the lid portions 102 can be performed by the reagent container lid opening/closing device 129 with a small load. Even in the case where the lid is not able to be opened due to manufacturing defects or the like of the reagent container 101 or the lid portion 102, it is possible to recognize that the lid portion 102 is not able to be opened when the operator sets the reagent container 101 in the reagent container lid half-open mechanism, which can prevent the reagent container 101 in which the lid portion 102 is not be able to be opened from being charged.

Figure 8:
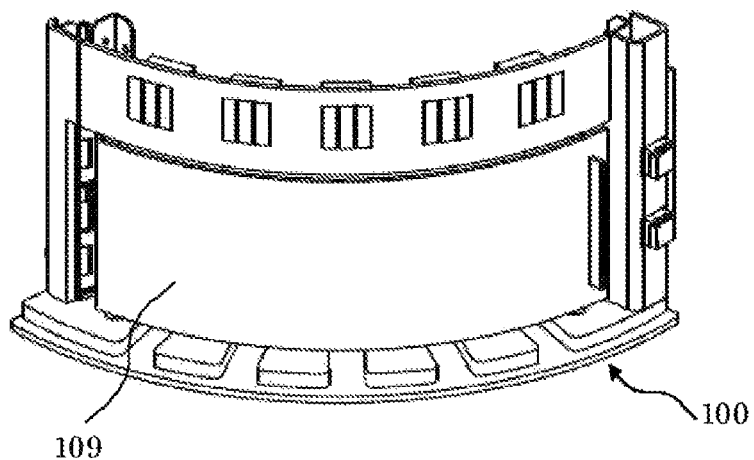
FIG. 8 is a perspective view showing the reagent container lid half-open mechanism according to the present invention.
Figure 9:
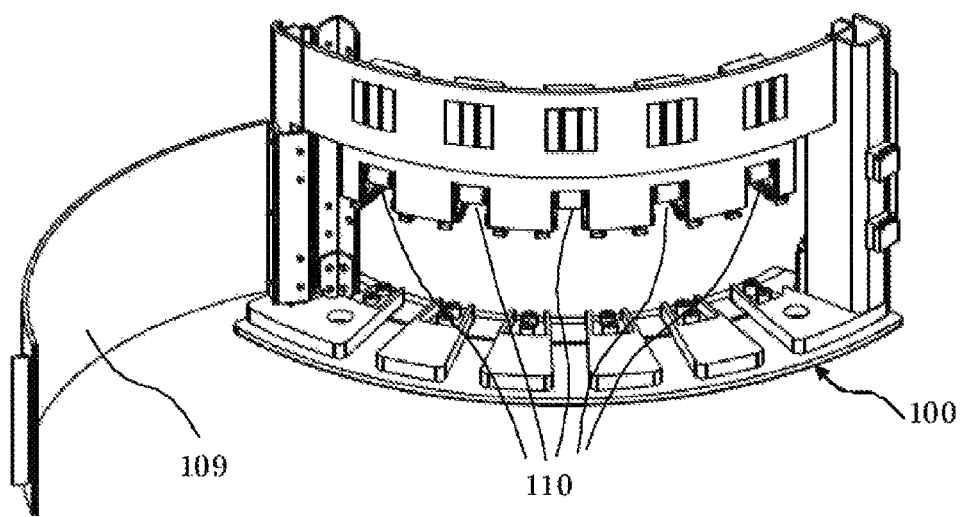
FIG. 9 is a perspective view of the reagent container lid half-open mechanism according to the present invention, showing a state where a cover is opened.

FIG. 8 and FIG. 9 show the entire diagrams of the reagent container lid half-open mechanism 100 according to the present invention.

FIG. 8 shows a state in which a cover 109 of the reagent container lid half-open mechanism 100 is closed. As the reagent container lid half-open mechanism 100 is provided on the front side of the reagent loader mechanism 104, the cover 109 is provided so that the operator is not able to have access to the inside of the reagent container lid half-open mechanism 100 in a state where the reagent loader mechanism 104 is in the bottom position.

FIG. 9 shows a state where the cover 109 is opened. It is possible to have access to the reagent loader mechanism 104 and the reagent container lid half-open mechanism 100 by opening the cover 109. In the embodiment, five reagent containers can be set on the reagent roader mechanism 104. Accordingly, five mechanical elements 110 for allowing the lids of the reagent containers to be the half-open state are provided so as to correspond to positions of respective slots in the reagent loader mechanism 104. In order to facilitate the setting of reagents by the operator, a guide portion having a groove is provided in front of the reagent container lid half-open mechanism 100 so that the reagent containers are slide and carried in/out with respect to the slots of the reagent loader mechanism 104.

Figure 10:
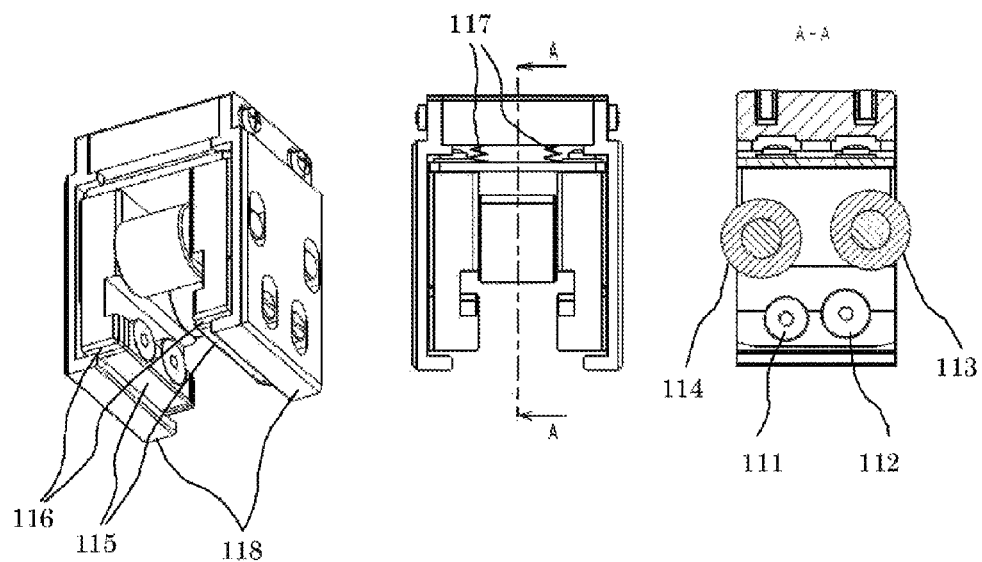
FIG. 10 is a view showing a mechanical element forming a half-open state of the lids of the reagent container in the reagent container lid half-open mechanism according to the present invention.

FIG. 10 shows the details of a structure of the mechanical elements 110 for allowing the lid portions 102 of the reagent container 101 to be in the half-open state. The mechanical element 110 is provided in an upper part of the reagent container lid half-open mechanism 100, including a small roller 111, a middle roller 112, an exit-side large roller 113, an entrance-side large roller 114, a reagent container shoulder holder 115, springs 117, upper and lower guides 118 and so on, which are symmetrically provided.

Figure 11:
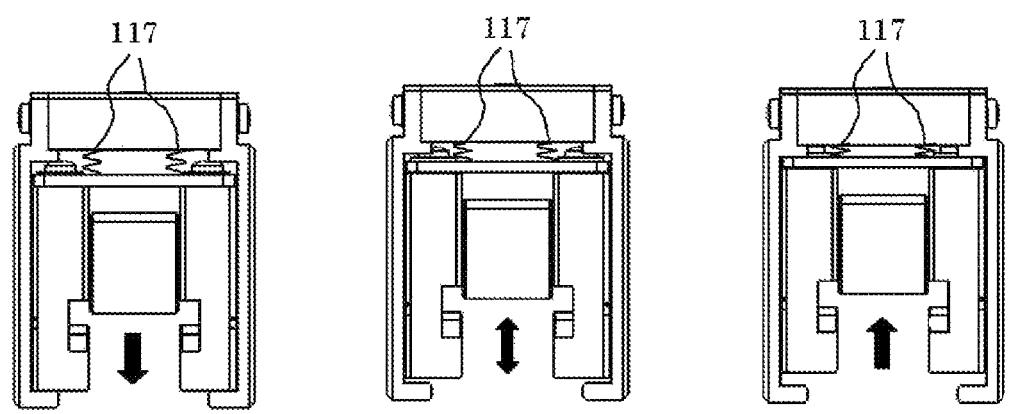
FIG. 11 is a view showing the mechanical element forming the half-open state of the lids of the reagent container in the reagent container half-open mechanism according to the present invention, showing a state where the mechanism is capable of moving upward and downward.

FIG. 11 is a view showing functions of the springs 117. The small roller 111, the middle roller 112, the exit-side large roller 113, the entrance-side large roller 114, the shoulder holder 115 of the mechanical element 110 are regarded as a unit (hereinafter, a unit portion is referred to as a mechanical element movable portion), which can vertically move along the upper and lower guides 118 by assembling the springs 117 inside the mechanical element 110. Functions of respective members will be explained later.

The reagent container lid half-open mechanism 100 is arranged above the reagent cooler 105 as well as in front of the reagent loader mechanism 104 as shown in FIG. 1. In the procedure in which the reagent container 101 the lid portions 102 of which are completely closed is set in the reagent container lid half-open mechanism 100 and is inserted into the reagent loader mechanism 104, the lid portions 102 of the reagent container 101 are allowed to be in the half-open state. Specifically, a method of allowing the lids to be in the half-open state by the reagent container lid half-open mechanism 100 will be explained by using cross-sectional views taken along a direction perpendicular and parallel to a direction in which the reagent container 101 is charged to the apparatus.

In the apparatus according to the embodiment, the reagent container 101 is charged so that the hinge portions of the lid portions 102 face the back side of the reagent loader mechanism 104. The operator pushes the reagent container 101 through the reagent lid half-open mechanism so as to be mounted on each slot of the reagent loader mechanism 104. At this time, the reagent container lids are half opened by the mechanical element 110 in accordance with the pushing movement of the reagent container 101. Hereinafter, FIG. 12 to FIG. 16 show states where the reagent container 101 is moved from left to right on the paper and the reagent is charged into the slot of the reagent loader mechanism 104.

Figure 12:
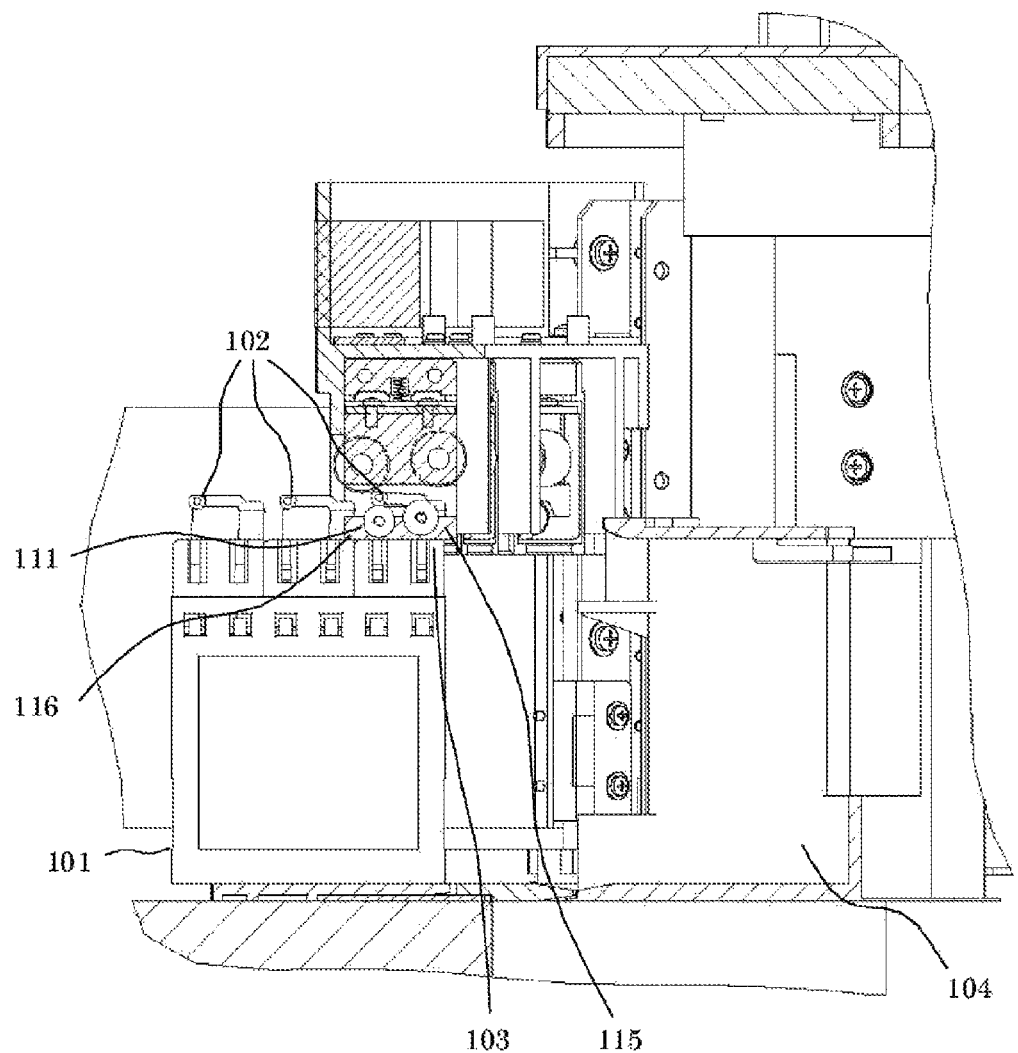
FIG. 12 is a cross-sectional view showing a structure of a vicinity of the reagent container lid half-open mechanism of the automatic analyzer according to the embodiment of the present invention, showing a state where the first lid of the reagent container is passing through the first roller on a lower side of the reagent container lid half-open mechanism.

FIG. 12 is a view showing a first stage for releasing the sealed state. First, the operator moves the reagent container 101 in the horizontal direction in a state where the shoulder 103 of the reagent container 101 contacts a lower surface of the reagent container shoulder holder 115. Then, a circumferential portion of the small roller 111 positioned in the lower side of the lid contacts a lower surface of the projection provided in the lid portion 102. When the reagent container 101 is further pushed in toward the reagent loader mechanism 104 in the above state, an upward force acts on the projection by the inclination of the circumferential portion of the small roller 111, which can open the lid portion 102 of the reagent container 101 to the uppermost part of the small roller 111. At this time, friction generated between the small roller 111 and the lid portion 102 can be reduced as the small roller 111 rotates. The force in the perpendicular direction can be increased by reducing an angle at which the small roller 111 contacts the lid portion 102 to be as small as possible even when the pushing force in the horizontal direction is small. That is, the arrangement of the roller is adjusted so that the lower part of the lid portion 102 of the reagent container contacts the position closer to the uppermost part of the roller, thereby pushing the reagent container into the automatic analyzer with a lighter force.

Figure 13:
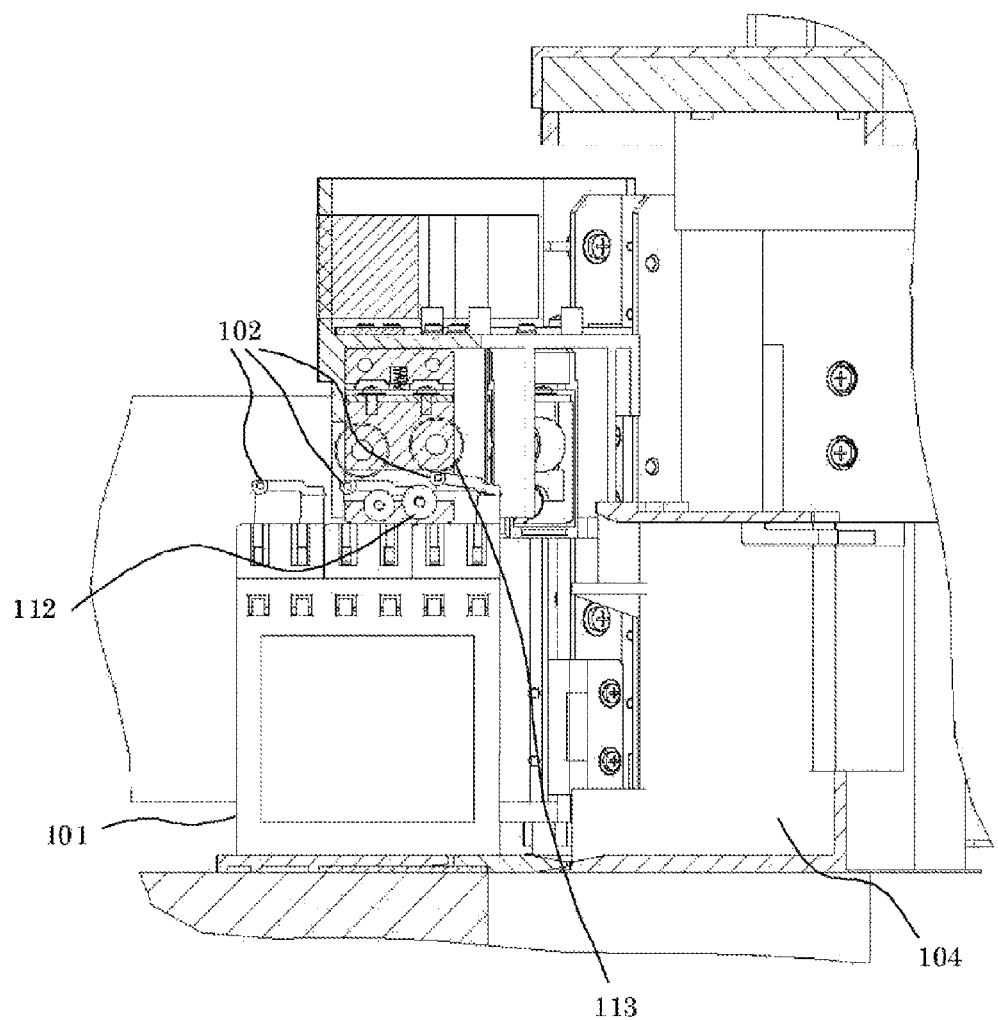
FIG. 13 is a cross-sectional view showing a structure of a vicinity of the reagent container lid half-open mechanism of the automatic analyzer according to the embodiment of the present invention, showing a state where the first lid of the reagent container is passing through the second roller on the lower side of the reagent container lid half-open mechanism.
Figure 14:
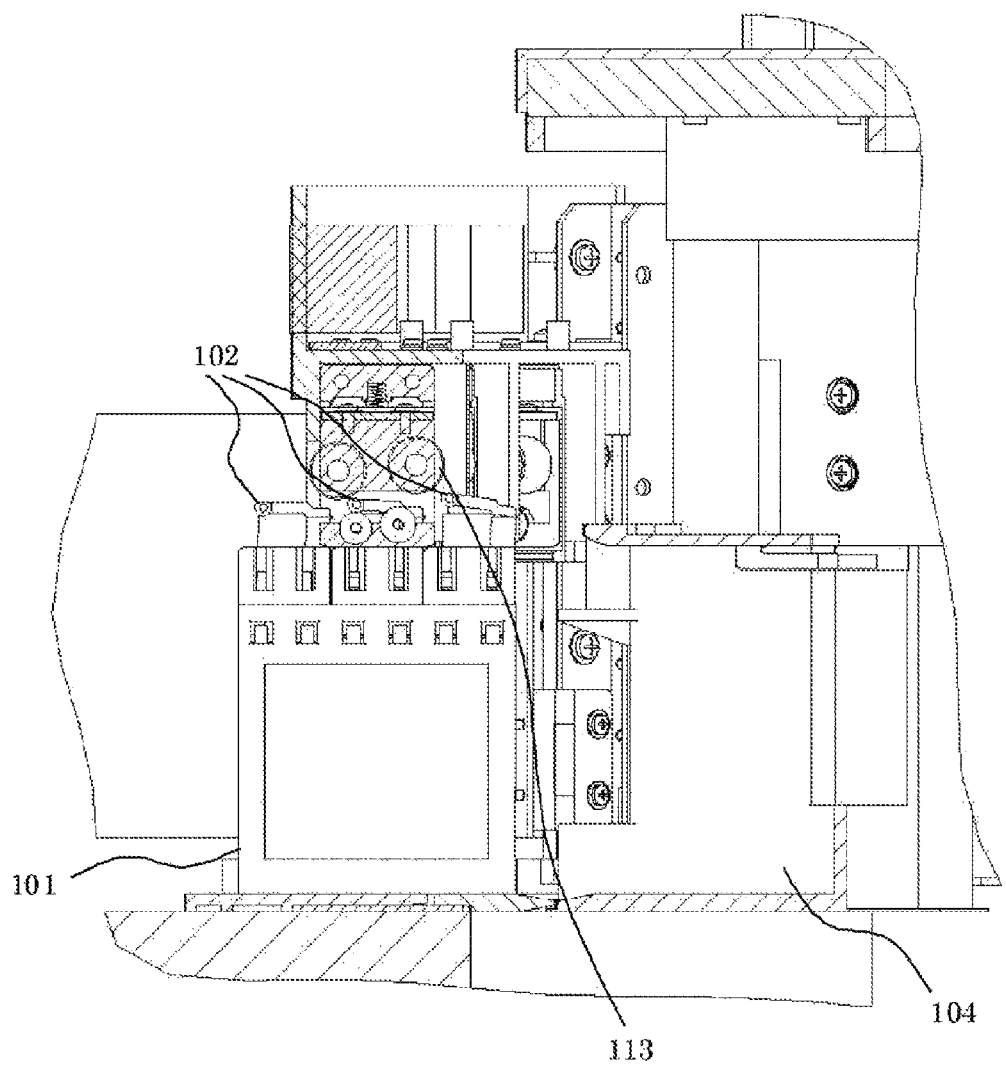
FIG. 14 is a cross-sectional view showing a structure of a vicinity of the reagent container lid half-open mechanism of the automatic analyzer according to the embodiment of the present invention, showing a state where the second lid of the reagent container is passing through the first roller on the lower side of the reagent container lid half-open mechanism.
Figure 15:
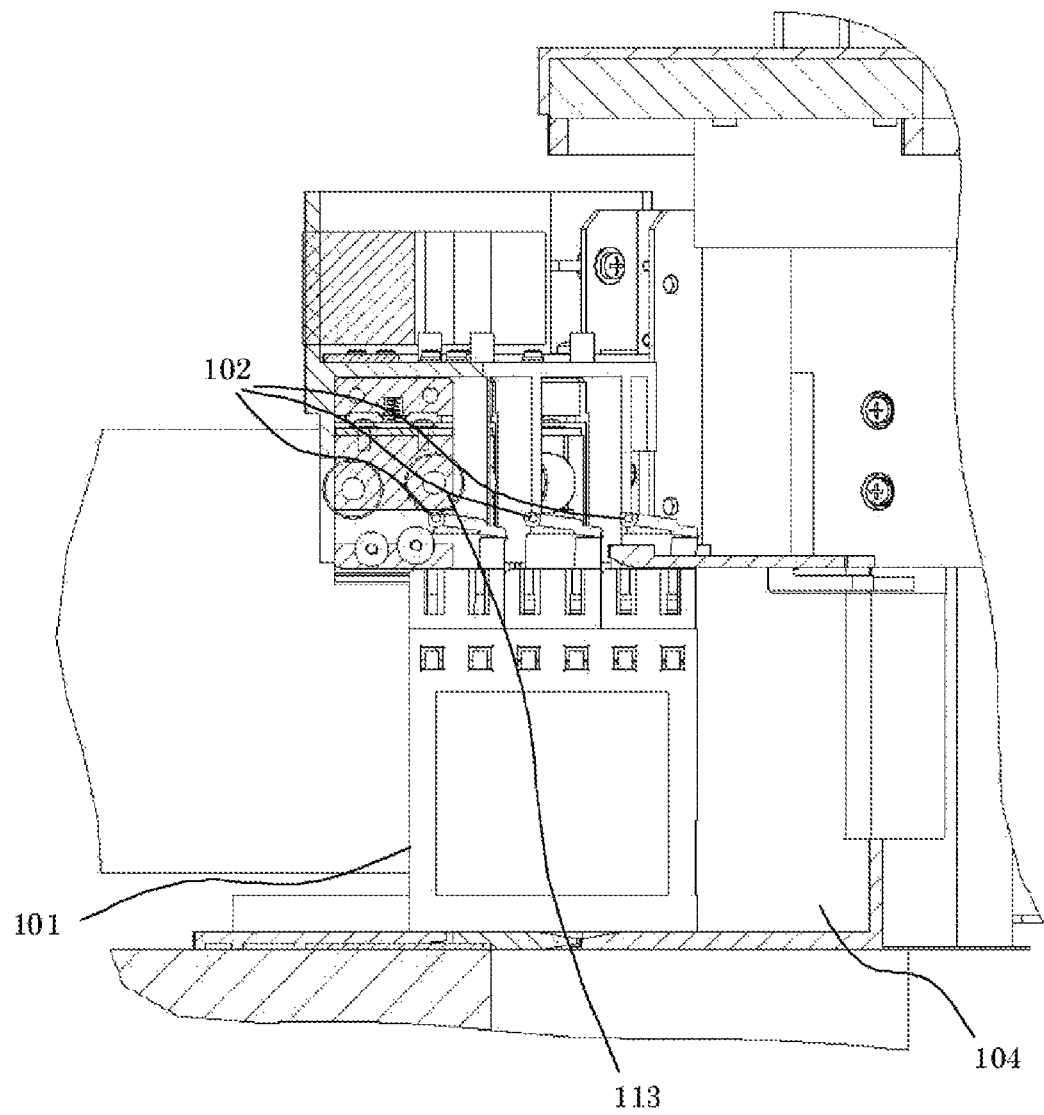
FIG. 15 is a cross-sectional view showing a structure of a vicinity of the reagent container lid half-open mechanism of the automatic analyzer according to the embodiment of the present invention, showing a state where all the three lids of the reagent container are passing through the second roller on the lower side of the reagent container lid half-open mechanism.

FIG. 13 is a view showing a second stage for releasing the sealed state. When the reagent container 101 is further pushed from the state shown in FIG. 12, the projection of the lid portion 102 contacts the middle roller 112 positioned in the back of the small roller 111. When the reagent container 101 is continued to be pushed, an opening angle of the lid portion 102 can be increased by the middle roller 112 having a larger diameter than the small roller 111. When the reagent container 101 is further continued to be pushed, the remaining lid portions 102 can be also opened similarly as shown in FIG. 14 and FIG. 15.

However, a space is provide above the small roller 111 and the middle roller 112 so as to pass with a margin when the lid portions 102 are opened, and heights of the opened lid portions 102 by both rollers are not always constant due to the reaction occurring when the lid portions 102 are opened. Accordingly, the exit-side large roller 113 is provided above the exit of the mechanical element 110 for making the heights of the opened lid portions 102 to be constant. The lid portions 102 the sealed state of which is released by the small roller 111 and the middle roller 112 are pushed from above to be the constant height by the exit-side large roller 113, thereby making the distance between the shoulder 103 of the reagent container 101 and the lid portions 102 to be constant, namely, the heights of the opened lid portions 102 are made to be constant.

Figure 16:
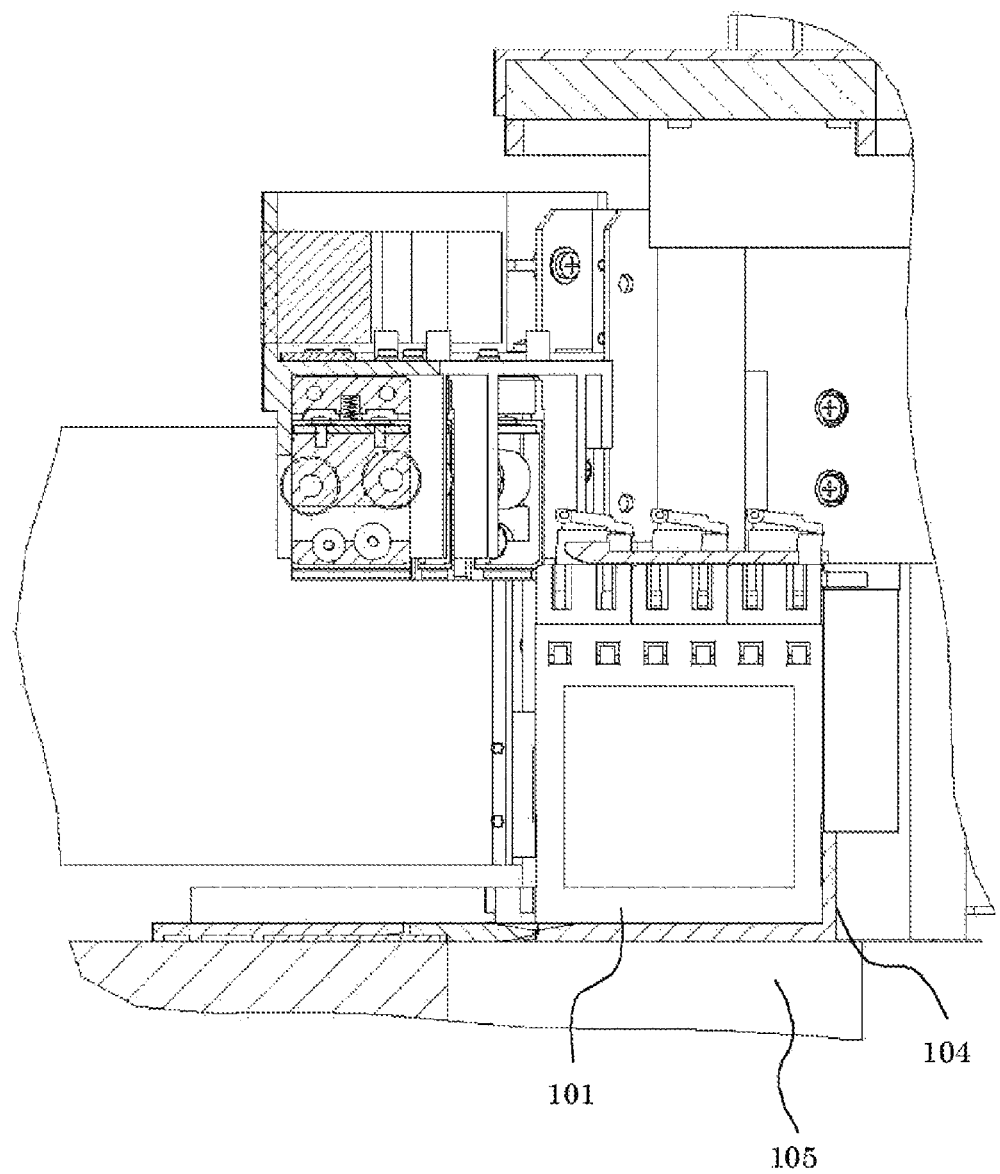
FIG. 16 is a cross-sectional view showing a structure of a vicinity of the reagent container lid half-open mechanism of the automatic analyzer according to an embodiment of the present invention, showing a state where the reagent container is pushed to the reagent setting section.

The reagent container can be charged into the reagent loader mechanism 104 as shown in FIG. 16 by further pushing the reagent container 101. After the reagent container 101 is charged into the reagent loader mechanism 104, the reagent loader mechanism 104 is moved downward to house the reagent container 101 inside the reagent cooler 105. After that, the reagent container 101 is moved from the reagent loader mechanism 104 by movements of respective mechanisms inside the reagent cooler 105 to be used in the analysis.

Technically speaking, the reagent containers are assumed to have variations in size to some degree. The springs 117 are assembled inside the mechanical element 110 as described above, thereby allowing the upper and lower movements of the mechanical element movable portion, and the lids of the reagent containers can be positively half opened even when the reagent containers 101 have some variations in height. That is, the initial position of the mechanical element movable portion is the bottom position as being pushed by the springs 117, however, when the reagent container 101 is pushed, the shoulder 103 abuts on a taper 116 of the shoulder holder 115, and the mechanical element movable portion moves upward by further pushing, then, the shoulder 103 of the reagent container 101 can contact the lower surface of the shoulder holder 115 to thereby push the container.

The reagent container lid half-open mechanism 100 according to the invention also has a function of sealing the reagent container lids at the time of discharging the reagent container 101 from the apparatus.

Figure 17:
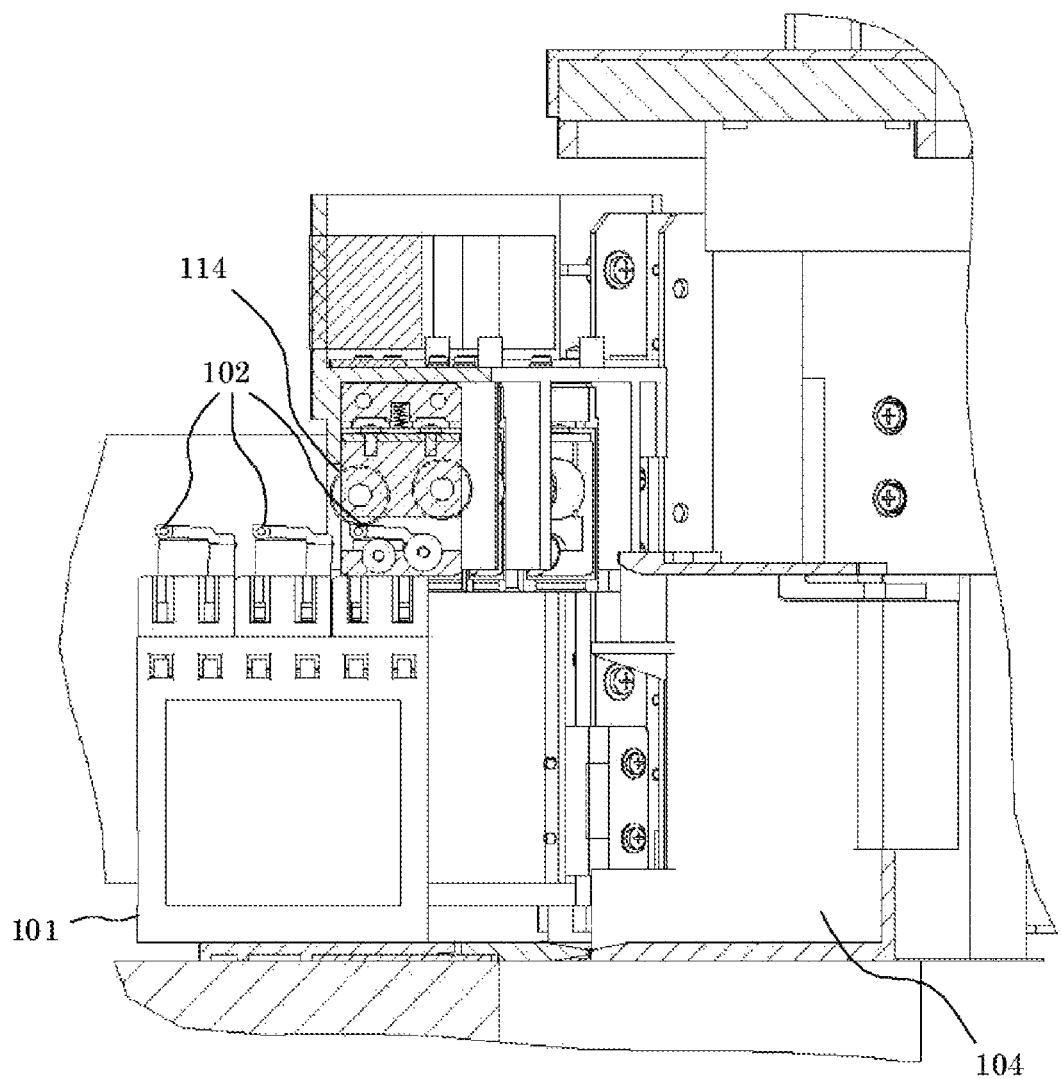
FIG. 17 shows a state where all the three lids of the reagent container are closed by being pushed by a left roller on an upper side of the reagent container lid half-open mechanism.

FIG. 17 is a view showing a case of sealing a half-open lid.

When the reagent container 101 is discharged from the apparatus, first, the reagent container 101 to be discharged is moved to the reagent loader mechanism 104 by the mechanism inside the reagent cooler 105. After that, the reagent loader mechanism 104 is moved upward, and the operator takes the reagent container 101 mounted on the reagent loader mechanism 104 out to the outside of the apparatus by manual through the reagent container lid half-open mechanism 100.

At the time when the reagent container 101 is discharged to the outside of the reagent cooler by the reagent loader mechanism 104, the lid portions 102 of the reagent container 101 are half opened. If the reagent container 101 is discharged in the half-open state, the reagents remaining inside the reagent container 101 may be spilled in case where the reagent container 101 is accidentally knocked over. Accordingly, the entrance-side large roller 114 is installed above the entrance side of the mechanical element 110 at a slightly lower position than the exit side. The half-opened lid portions 102 are pushed by the entrance-side large roller 114 when discharging the reagent container 101, thereby inserting the sealing members 139 into the openings 138 to be sealed. Accordingly, the danger that the reagents are spilled after the discharge can be reduced. It is not always necessary to seal the openings 138 completely when discharging the reagent container. For example, positions and angles of the lid portions can be adjusted to positions where the lid portions 102 cover the openings 138 by pushing the lid portions 102 by the entrance-side large roller 114. As part of the sealing members 139 is inserted into the opening 138, the discharge can be performed in a state where the lid portions are not easily opened as compared with the half-open state but not reaching the sealed state. In this case, the reagent container can be discharged with a smaller force and the reagent is not spilled even when the reagent container is knocked over.

The mechanical element 110 of the reagent container lid half-open mechanism 100 according to the present invention adopts the system in which the lid portions 102 of the reagent container 101 are opened in two stages by the small roller 111 and the middle roller 112. When a contact angle between the projection of the lid portion 102 and the roller is small, the upward force to open the lid portion 102 can be increased even when the force of pushing the reagent container 101 is small. When many rollers are provided, a distance in which the lid portions 102 move in the perpendicular direction becomes small inversely, there is a case where diameter sizes of respective rollers are not able to be sufficiently increased due to space limitations. The rollers with two-stage sizes are adopted in the present invention because of size limitations of a space between the lid portions 102 and the shoulder 103 of the reagent container 101, however, one large roller may be adopted as one stage structure when a larger size can be secured. Conversely, when only a smaller size can be secured, more rollers may be arranged as structures of two or more stages.

In the present invention, guides 119 parallel to the inserting direction are provided on a lower surface of the charging portion at respective inserting positions so as to facilitate the insertion and discharge of the reagent container 101, however, it is not always necessary to provide the guides 119.

In the embodiment, the work is performed by opening the cover 109 as shown in FIG. 1 at the time of charging and discharging the reagent container 101. The cover 109 is configured to laterally open, however, covers in any forms such as a longitudinally opening, a double opening and a lateral sliding opening may be adopted. It is also preferable to provide a structure in which the reagent loader mechanism 104 is not moved when the cover is open by installing an open/close detection sensor (not shown) or the like for the cover 109, and preferable to provide a switch which starts the movement of the reagent loader mechanism 104 by closing the cover 109 for avoiding a risk of pinching a hand of the operator during the movement of the reagent loader mechanism 104.

Five slots are provided in the reagent loader mechanism 104 of the embodiment, and at most five reagent containers 101 can be charged or discharged in a single work, however, it is not always necessary to set the reagent containers in all slots, and less than five containers may be charged or discharged. The reagent loader mechanism 104 may have a device structure capable of mounting less than five or five or more reagent containers.

In the embodiment, the structure in which the reagent loader mechanism moves upward and downward and the slots whereby the reagent containers 101 can be radially set on the reagent loader mechanism 104 are provided is adopted, however, the present invention is not limited to this. For example, it is also preferable to adopt a robot arm as a reagent loader mechanism, and to adopt a system in which reagent containers put in predetermined charging positions are chucked and carried into the slots of the reagent disc by the robot arm. In this case, a mechanism corresponding to the reagent container lid half-open mechanism 100 according to the embodiment may be provided in a position where the reagent containers to be carried into the reagent cooler are placed for being chucked by the robot arm, and the reagent containers can be half opened when the reagent containers are set.

Figure 18:
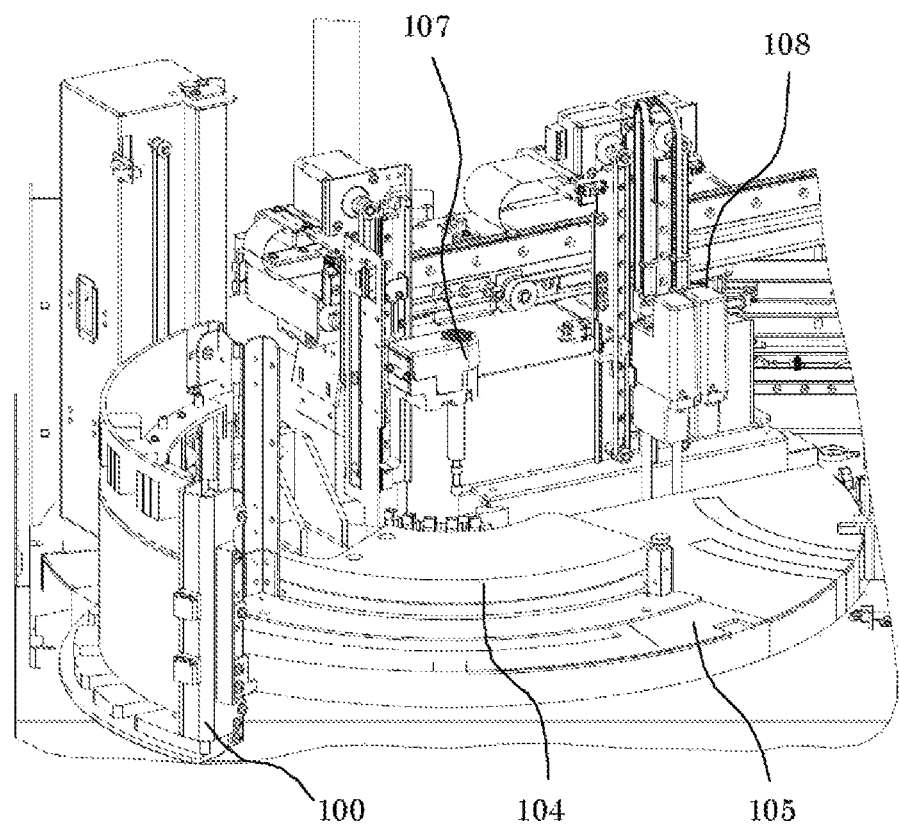
FIG. 18 is a perspective view showing a structure of a vicinity of a reagent container lid half-open mechanism of the automatic analyzer according to an embodiment of the present invention, showing a state where the entire reagent container lid half-open mechanism is opened and an access to a magnetic particle stirring device, a reagent dispensing device and so on is allowed.

FIG. 18 shows a structure in which the entire reagent container lid half-open mechanism 100 can be opened and closed by rotation with a left end as a rotation axis. When the reagent container lid half-open mechanism 100 can be opened and closed, the operator can easily have access to the magnetic particle stirring device 107, the reagent dispensing device 108 and the like provided on the back side of the apparatus when the operator performs cleaning or maintenance.

Embodiment 2

In the embodiment, an example of an apparatus capable of avoiding or reducing the frequency of occurrence of problems generated by operation failures at the time of charging the reagent container 101 by the operator will be explained in addition to the function of Embodiment 1. Although a mechanism capable of automatically charging the reagent containers 101 for avoiding the operator dependence may be added, only the case where the operator charges the reagent container 101 is considered.

As some pushing force will be necessary at the time of charging the reagent container in the reagent loader mechanism 104 when the reagent container lid half-open mechanism 110100 is provided, the operator may falsely recognize that the reagent container is placed on the reagent loader mechanism 104 through the reagent container is not placed thereon because of insufficient pushing. For example, in the case where the operator falsely recognizes that the reagent container has been charged, and leaves the apparatus in the state shown in FIG. 15, there arise problems that the reagent container 101 is pinched by neighboring members and the following processing is hindered or the members are damaged when the reagent mechanism 104 is moved downward while maintaining the above state.

The apparatus according to the embodiment has any of the following functions and combinations thereof.

Figure 19:
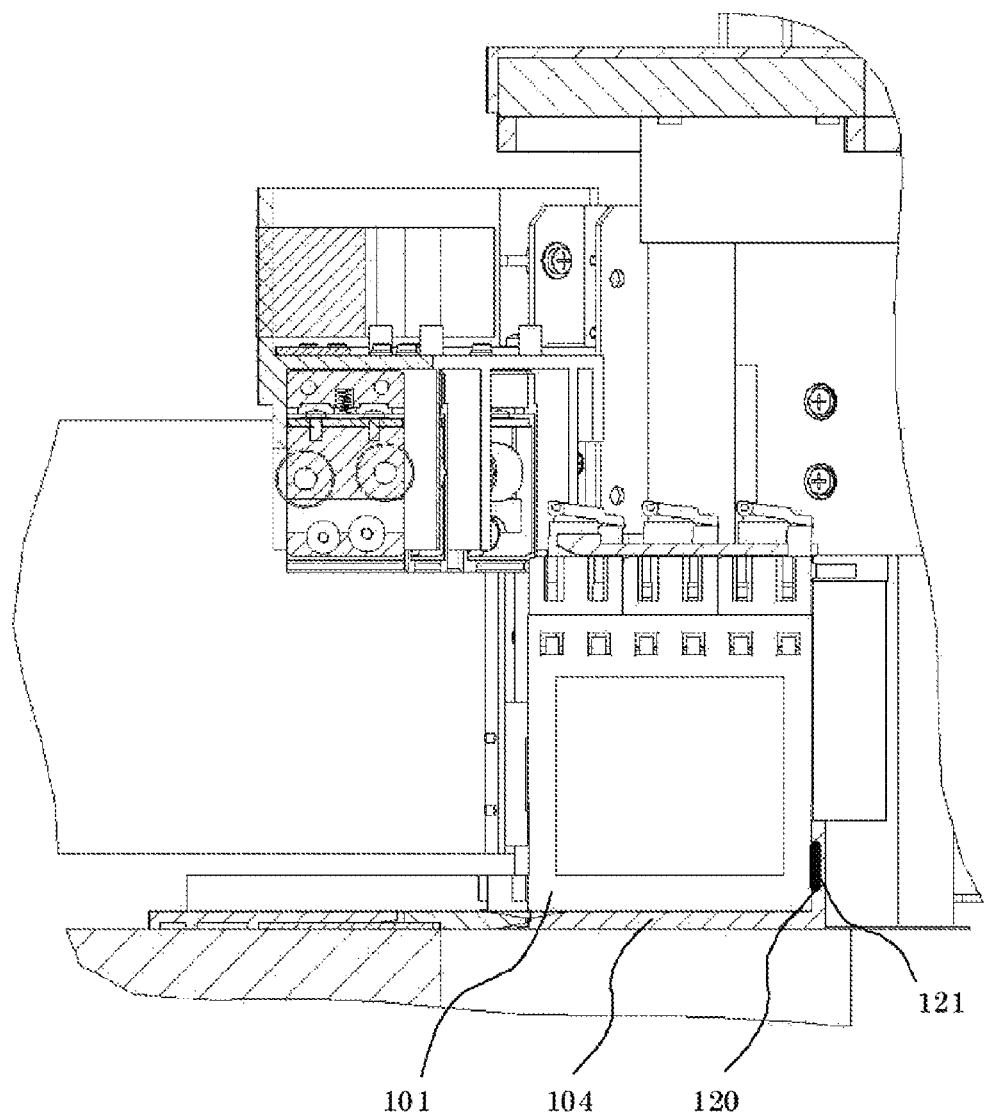
FIG. 19 is a cross-sectional view showing a structure of a vicinity of the reagent container lid half-open mechanism of an automatic analyzer according to an embodiment of the present invention, showing a state where the reagent container is pushed to reach a contact sensor in the reagent setting section.

(a) To positively insert the reagent container 101 to a position not to be pinched
(b) To detect that the reagent container 101 is in a position where the container is pinched
(c) To detect that the reagent container 101 has been pinched and stop the operation when the reagent setting section 101 moves downward and the reagent container is pinched FIG. 19 includes a contact sensor 121 on a backmost wall 120 in the reagent loader mechanism 104 on which the reagent container 101 abuts in response to the above (a). The operator is informed of the contact of the reagent container 101 with respect to the contact sensor 121 by emitting an indicator such as an LED at a position where the container is charged, then, the reagent loader mechanism 104 is moved downward. As the operator can check whether the pushing to the reagent loader mechanism is sufficient or not by providing the function, the frequency of occurrence of pinching the reagent container can be reduced.

Figure 20:
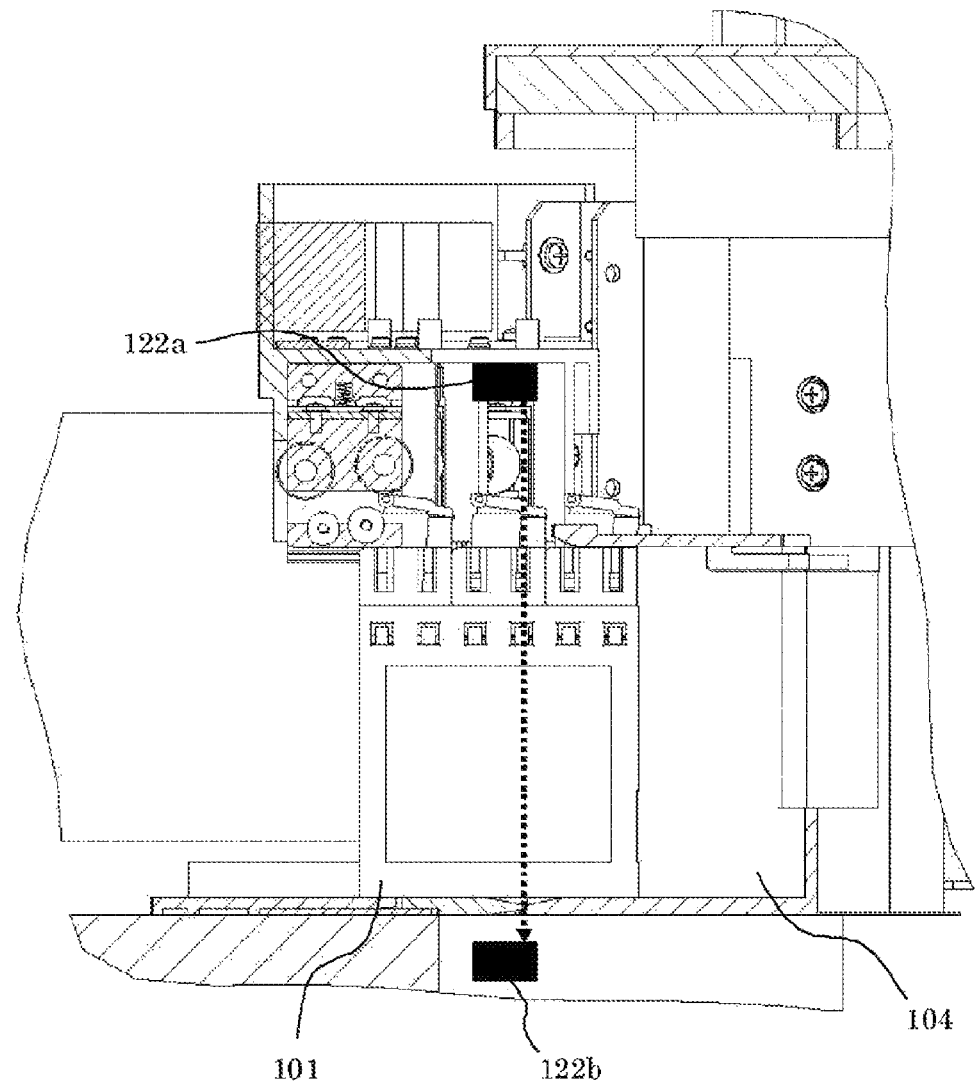
FIG. 20 is a cross-sectional view showing a structure of a vicinity of the reagent container lid half-open mechanism of the automatic analyzer according to the embodiment of the present invention, showing a state where the reagent container is detected by a transmission type sensor in a position where the reagent container is pushed halfway.

In FIG. 20, sensors capable of detecting that the reagent container 101 is in a position where the reagent container 101 is pinched such as transmission type sensors 122a (light transmission side) and 122b (light receiving side) are installed in response to the above (b). The transmission type sensors 122a and 122b are linearly arranged in positions not blocking optical paths in a state where the reagent container 101 is placed on the reagent loader mechanism 104. In the case where light from the transmission type sensor 122a (light transmission side) does not reach the sensor 122b (light receiving side), it is possible to detect that the reagent container is in a position where the container is pinched. In that case, the movement of the reagent loader mechanism 104 is not allowed.

Figure 21:
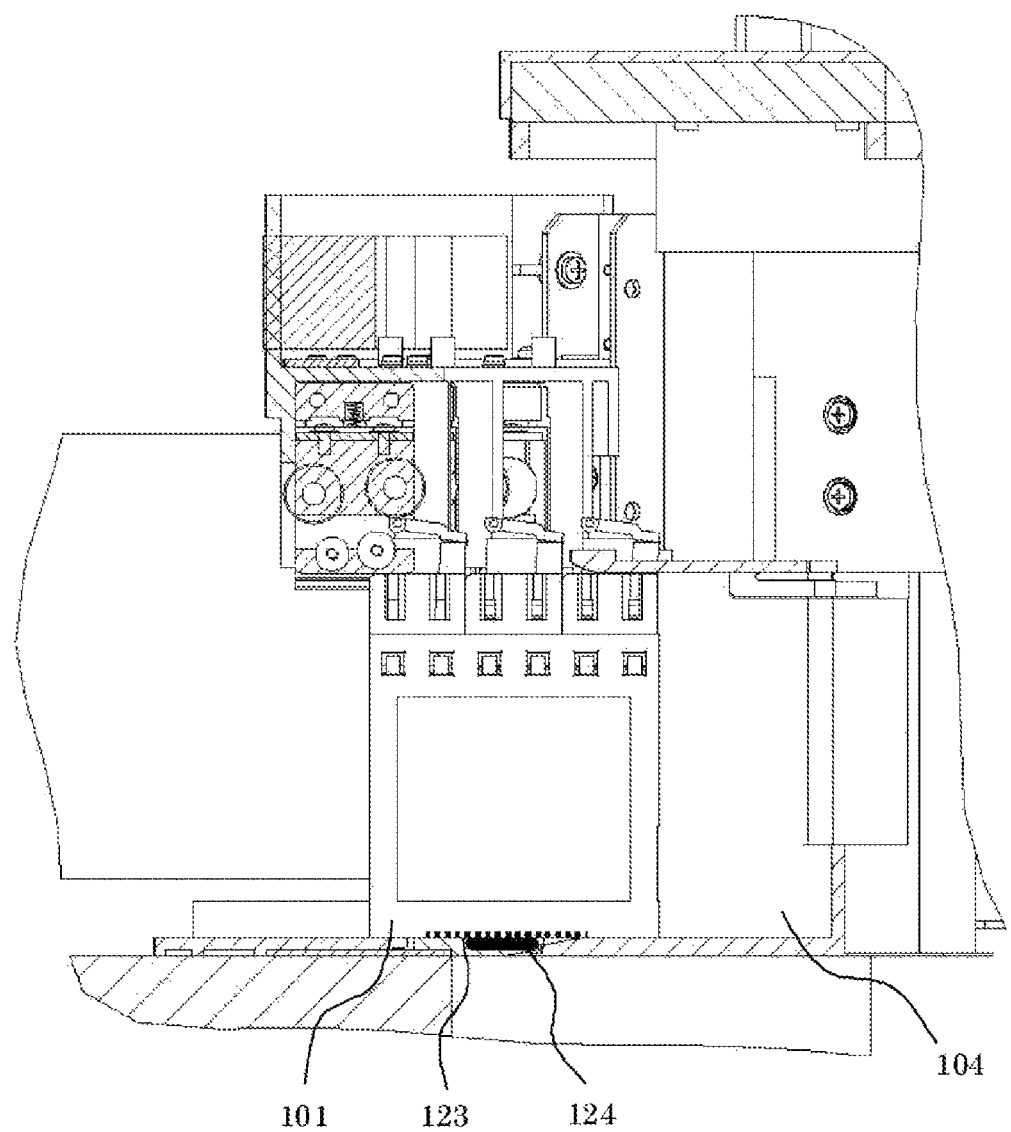
FIG. 21 is a cross-sectional view showing a structure of a vicinity of the reagent container lid half-open mechanism of the automatic analyzer according to the embodiment of the present invention, showing a state where pinching of the reagent container is detected by a pinching sensor in a position where the reagent container is pushed halfway.

In FIG. 21, a pinching sensor 124 for detecting that the reagent container 101 is pressed by something is installed on a charging path bottom surface 123 of the reagent container 101 in response to the above (c). As the state where the reagent container 101 is pinched by the reagent loader mechanism 104 can be detected by providing the pinching sensor 124, therefore, the apparatus can stop the downward movement of the reagent loader mechanism 104 when the apparatus detects the pinching.

REFERENCE SIGNS LIST

100 reagent container lid half-open mechanism
101 reagent container
102 lid portion
103 shoulder portion
104 reagent setting section
105 reagent cooler
106 stirring and dispensing position
107 magnetic particle stirring device
108 reagent dispensing device
109 cover
110 mechanical element
111 small roller
112 middle roller
113 exit-side large roller
114 entrance-side large roller
115 shoulder holder
116 taper
117 spring
118 upper and lower guide
119 guide (discharging path of reagent container)
120 wall (backmost part of reagent container setting section)
121 contact sensor
122a transmission type sensor (light transmission side)
122b transmission type sensor (light receiving side)
123 charging path bottom surface
124 pinching sensor
125 hinge
126 projection
127 reagent disc
128 reagent container moving device
129 reagent container lid opening/closing device
130 magazine
131 reaction container/sample dispensing chip conveyance device
132 sample dispensing device
133 sample rack
134 reaction vessel
135 reaction liquid stirring device
136 reaction liquid cleaning device
137 detecting section
138 opening
139 sealing member

The invention claimed is:

1. An automatic analyzer comprising:
   a detecting section for measuring a fixed amount of measurement target component in reaction liquid;
   a reagent storage storing reagent containers and forming an enclosed housing, said reagent storage configured to store the reagent containers,
   reagent containers, each having a main body housing a reagent used for analysis, an opening provided on a top of the main body, and a lid portion having a sealing member for sealing the opening by being inserted into the opening;
   a lid opening/closing mechanism provided inside the reagent storage enclosure that opens and closes lids of the reagent container set in the reagent storage;
   a reagent loader mechanism loading having a reagent setting section with a plurality of slots, each slot to house at least one reagent container;
   a mechanism to partly open a reagent container having a plurality of mechanical elements which are respectively provided for each slot to partly open at least one reagent container by removing the sealed member from the opening of the at least one reagent container, whereby the reagent container lid is opened to a predetermined angle by the mechanism to partly open the reagent container by an operation of placing the reagent container into the respective slots of the reagent setting section, wherein when the reagent loader mechanism moves between an open position where the mechanism to partly open the container is accessible and a closed position inside the reagent storage; and
   a processing mechanism for executing dispensing or stirring processing of the at least one reagent stored inside the reagent storage.

2. The automatic analyzer according to claim 1, wherein the mechanism to partly open the reagent container lid portion includes a first roller opening the sealing member of the lid portion from the opening by contacting the lid portion from below, and
   a second roller making an opening angle of the lid portion be a predetermined angle by contacting the lid portion opened by the first roller from above.

3. The automatic analyzer according to claim 2, wherein a position where the lid portion contacts the first roller is a vicinity of the uppermost part of the first roller.

4. The automatic analyzer according to claim 1, wherein a plurality of first rollers are provided.

5. The automatic analyzer according to claim 1, further including resilient members holding the mechanism to partly open the reagent container lid portion so as to permit movement upward and downward.

6. The automatic analyzer according to claim 1, wherein the reagent loader mechanism has a function of discharging the reagent container inside the reagent storage, and
   the mechanism to partly open the reagent container lid portion has a function of inserting the sealing member into the opening to make the opening be a sealed state by an operation of taking the reagent container out from the reagent loader mechanism.

7. The automatic analyzer according to claim 6, wherein the mechanism to partly open the reagent container lid portion includes a third roller adjusting a position of the lid portion so as to cover the opening by contacting the lid portion of the reagent container taken out from the reagent loader mechanism from above.

8. The automatic analyzer according to claim 1,
wherein the mechanism to partly open the reagent container lid portion is movably mounted to an outside part of the reagent storage so the mechanism is movable to a position permitting access thereto for cleaning and/or maintenance.

9. The automatic analyzer according to claim 1,
wherein the reagent loader mechanism has a means for detecting that the reagent container is positively inserted into reagent loader mechanism.

10. The automatic analyzer according to claim 1,
wherein the reagent loader mechanism has a means for detecting a contact position before the reagent setting section operates when there is a possibility that the reagent container contacts neighboring members by operating the reagent loader mechanism in a state where the reagent container is not positively pushed into the reagent setting section.

11. The automatic analyzer according to claim 1,
further including means for detecting a contact as well as stopping an operation of the reagent loader mechanism before the contact position is damaged when the reagent loader mechanism operates and the reagent container contacts neighboring members in a state where the reagent container is not positively pushed into the reagent setting section.

\* \* \* \* \*